(12) United States Patent
Hur

(10) Patent No.: US 6,177,755 B1
(45) Date of Patent: Jan. 23, 2001

(54) AIR COOLED ULTRASONIC APPARATUS

(76) Inventor: Ben Hur, 533 E. Lemon Ave., Arcadia, CA (US) 91006

( * ) Notice: Under 35 U.S.C. 154(b), the term of this patent shall be extended for 0 days.

(21) Appl. No.: 09/426,565

(22) Filed: Oct. 22, 1999

(51) Int. Cl.$^7$ ....................................................... H02N 2/00
(52) U.S. Cl. .............. 310/346; 310/323.18; 310/323.19; 310/341
(58) Field of Search ................... 310/323.12, 323.18, 310/341, 346, 323.19, 325

(56) References Cited

U.S. PATENT DOCUMENTS

| | | | |
|---|---|---|---|
| 3,694,675 | * 9/1972 | Loveday | 310/323.12 |
| 4,169,984 | 10/1979 | Parisi | 310/323 |
| 4,741,731 | * 5/1988 | Starck et al. | 604/22 |
| 4,828,052 | 5/1989 | Duran | 175/55 |
| 4,838,853 | 6/1989 | Parisi | 604/22 |
| 4,869,715 | 9/1989 | Sherburne | 604/22 |
| 5,955,823 | * 9/1999 | Nilsson et al. | 310/346 |

FOREIGN PATENT DOCUMENTS 2 000 470 * 1/1979 (GB) ............................... 310/323.18

OTHER PUBLICATIONS

Direct Cooling Technique for Quartz Deposition Monitors, IBM Technical Disclosure Bulletin, vol. 34, No. 7B; pp. 286–287, Dec. 1991.*

* cited by examiner

Primary Examiner—Thomas M. Dougherty
(74) Attorney, Agent, or Firm—John K. Park; Park & Sutton LLP

(57) ABSTRACT

An air cooled ultrasonic apparatus comprises a housing having an air inlet, an air outlet, a first periphery, and a second periphery. A plurality of first and second protrusions radially extend from the first and second peripheries. The housing houses a piezoelectric transducer means and an elongated horn which is operably supported by the first and second protrusions, so that a cooling air is supplied through the air inlet into the housing and discharged through the air outlet, thereby significantly enhancing effectiveness and efficiency for its application to medical, dental and plastic surgery as well as industrial use.

18 Claims, 3 Drawing Sheets

AIR COOLED ULTRASONIC APPARATUS

BACKGROUND OF THE INVENTION

This present invention relates to a ultrasonic apparatus. More particularly, this present invention relates to a highly effective air cooled ultrasonic apparatus adopting an air cooling system in replacement of a conventional water cooling system. The present invention is especially adapted as a precision medical device for medical, dental or plastic surgery but its application is not limited to the medical field.

Conventionally, an ultrasonic handpiece or apparatus generates a significant heat due to its high speed operation and a water cooling system is generally applied for cooling such an ultrasonic apparatus.

However, the peripheral surface of the hollow hole for the cooling water is limited and accordingly the cooling efficiency is not satisfactory to its user. Therefore, a prominent improvement is required for effectiveness and efficiency in a cooling system of the ultrasonic drilling machine.

When a cooling water is adopted to an ultrasonic machine, several disadvantages are clearly witnessed. First, since it is known that an impedance (Z) for water is incorporated in density ($\rho$) multiplied by velocity (c) or Z=$\rho \cdot$c, the impedance for water is significantly high, compared to an impedance for air. That is, it should be understood that Z (=$\rho \cdot$c) for water is larger than Z' (=$\rho' \cdot c'$) for air. Although pressure factor is considered, the impedance (Z') for air is neglectable. Specifically, it is known that an impedance Z (=412 (Pa/(m/s)) for air is 3,600 times less than impedance Z' ($1.48 \times 10^6$ (Pa)/(m/s)).

Second, when a water cooling system is employed, a cooling surface area (peripheral surface area of the hollow hole) is inevitably limited. That is, an ultrasonic energy becomes decreased in proportion that a cooling surface area becomes larger. This is because an energy transit circuit is influenced by the ratio of stress and thickness.

Third, it is troublesome to finish an operative tip end because the cooling water tends to undesirably leak through the tip end. Further, the variety for tip shapes is strictly limited since a priority should be placed on prevention of water leakage through the operative tip.

Therefore, it is an object of the present invention to provide an air cooled ultrasonic apparatus which is effectively cooled by air.

It is another object of the present invention to provide a wider cooling surface area in comparison to the conventional hollow hole for water cooling.

Still another object of the present invention is to enable a variety of operative tip shapes for the ultrasonic apparatus.

Additional objects, advantages, and novel features of the present invention will be set forth in the description that follows, and it is apparent that those skilled in the art may be learned by practice of the invention upon examination of the following. The objects and advantages of the invention may be realized and attained by means of the instrumentalities and combinations particularly pointed out in the appended claims.

SUMMARY OF THE INVENTION

To achieve the foregoing objects and other objects, as embodied and broadly described herein, a highly efficient air cooled ultrasonic apparatus according to the present invention for various precision applications such as medical, dental and plastic surgery comprises a housing, a piezoelectric transducer means, and an elongated horn.

The housing has an air inlet, an air outlet, a first periphery and a second periphery. A plurality of first and second protrusions radially extend from the first and second peripheries. The elongated horn has a first horn end and a second horn end, wherein the first horn end forms an operative tip, wherein the second horn end is attached to the transducer means and housed in the housing. Also, the elongated horn is operably supported by the first and second protrusions so that a cooling air can be supplied through the air inlet into the housing and discharged through the air outlet.

An improvement of the present invention comprises a housing having an air inlet, a horn cover having an air outlet, a first periphery and a second periphery, wherein the horn cover is engagedly attached to the housing. A plurality of first and second protrusions radially extend from the first and second peripheries.

Meanwhile, the first and second protrusions are respectively formed in embossed shape so as to create a laminar flow when the cooling air passes over the respective first and second protrusions. Each base of the plurality of first and second embossed protrusions comprises a front base end and a rear base end which are decrementally enlongated toward corresponding horn ends. Here, the second base end is elongated farther than the first base end.

The horn cover further comprises first and crimple zones, and wherein the first crimple zone is formed either between the first periphery and the second periphery or outside the second periphery toward the operative tip. Alternately, the first and second crimple zones may be formed outside the second periphery toward the operative tip.

In particular, the air inlet is formed through a rear end of the housing opposed to the operative tip, and the air outlet is formed through a peripheral opening between the operative tip and a front end of the housing. Also, it is preferred that the air outlet is formed adjacent to the front end of the housing.

The benefits of this inventions are numerous. First, the air cooling system applied to the air cooled ultrasonic apparatus is highly efficient compared to the prior art because a wider surface area between the elongated horn 14, the horn cover 21 and the housing 22 than the surface area of a conventional cooling water hollow hole formed though the horn, can be exposed to the cooling air, thereby enhancing cooling efficiency. Second, the present invention enables a cooling air to be controlled as low as a below zero Celsius degree, that is, below a freezing point, thereby maximizing a cooling effect. Third, various bits can be applied since the present invention has overcome the conventional water draining problem around the operative tip, and even the air outlet can be formed in a desired portion of the horn cover. Fourth, since impedance Z (=$\rho \cdot$c) for air is less than impedance Z' (=$\rho' \cdot c'$) for water (where, $\rho$ denotes density, c denotes velocity), that is, $\rho \cdot c < \rho' \cdot c'$ is satisfied, the cooling air enables a low c at a cold temperature without being influenced by atmospheric pressure, thereby further realizing better cooling performance.

Although the present invention is briefly summarized, the fuller understanding of the invention can be obtained by the following drawings, the detailed description and appended claims.

BRIEF DESCRIPTION OF THE DRAWINGS

The present invention will be better understood with reference to the accompanying drawings, wherein.

DETAILED DESCRIPTION OF THE PREFERRED EMBODIMENTS

With reference to the accompanying drawings, the air cooled ultrasonic apparatus according to the present invention will now be described.

Figure 1:
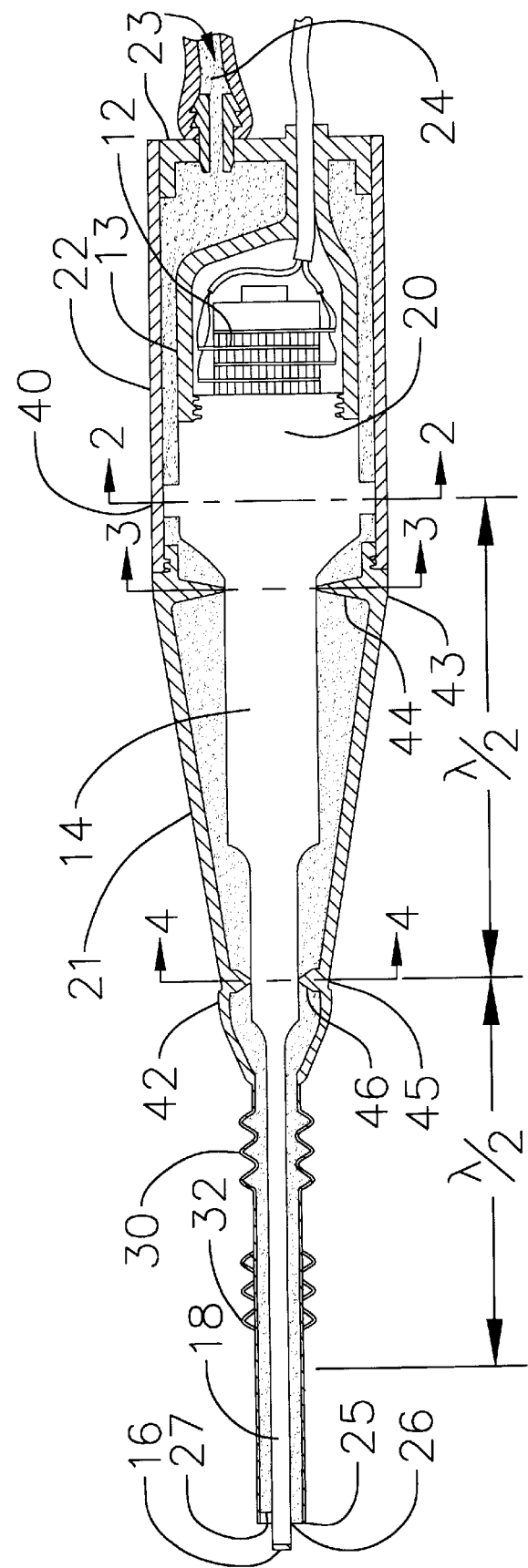
FIG. 1 is a cross-sectional view illustrating an air cooled ultrasonic apparatus according to this invention.

As shown in FIG. 1, the air cooled ultrasonic apparatus 10 comprises a piezoelectric transducer means 12 to generate an axial stroke through an elongated horn 14 toward an operative tip 16. The apparatus 10 also comprises the elongated horn 14 which has a first horn end 18 and a second horn end 20. The first horn end 18 serves as the operative tip 16 and the second horn end 20 is engagedly connected to the transducer means 12, wherein a bit (not shown) can be fixedly attached to the operative tip 16.

The piezoelectric transducer means 12 is sealingly covered by a shroud 13 which is also engaged to the second horn end 20. Here, a common form of the piezoelectric transducer means 12 can be a BLT (Boltclamped Langevin Type Transducer) composed of PZT (Piezoelectric Lead Zirconate Titanate Crystals).

Depending on purpose, the elongated horn 14 may be formed as an exponential type horn (not shown) or a stepped type horn as shown in FIG. 1. Also, the elongated horn 14 may be formed of a high strength material such as a titanium alloy or an aluminum alloy.

In an embodiment of the present invention, the housing 22 comprises an air inlet 24 formed adjacent to the shroud 13, and an air outlet 26 provided adjacent to the first horn end 18, wherein a cooling air is supplied through the air inlet 24 into the housing 22 and discharged through the air outlet 26 while cooling the apparatus 10 heated during its operation. The air inlet 24 is formed through a rear end 23 of the housing 22 opposed to the operative tip 16, and the air outlet 26 is formed through a peripheral opening 27 between the operative tip 16 and a front end 25 of the housing 22. Selectively, the air outlet 26 may be formed adjacent to the front end of the housing 22.

Meanwhile, the housing 22 is abuttingly attached to the elongated horn 14 at about two nodal points, a first nodal point 40 and a second nodal point 42. The nodal points 40, 42 denote those points on the elongated horn 14 that have the least vibration, where the amplitude of the sinusoidal wave of the ultrasonic wave generated by the piezoelectric transducer means 12 is the lowest.

Figure 2:
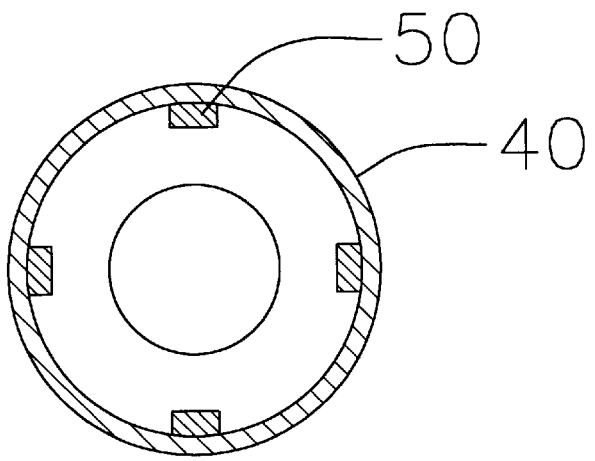
FIG. 2 is a cross-sectional view taken along line 2—2 of FIG. 1.

As shown in FIG. 2, a plurality of air openings 50 are formed at the first nodal point 40 and between the elongated horn 14 and the housing 22 so as to absorb horizontal vibration of the elongated horn 14 in the prior art and to further facilitate a cooling air communication in the present invention.

For a better performance, the housing 22 further comprises a first periphery 43 and a second periphery 45. A plurality of first protrusions 44 radially extend from the first periphery 43, and a plurality of second protrusions 46 radially extend from the second periphery 45, wherein the elongated horn 14 is operably supported by the first and second protrusions 44, 46.

Figure 3:
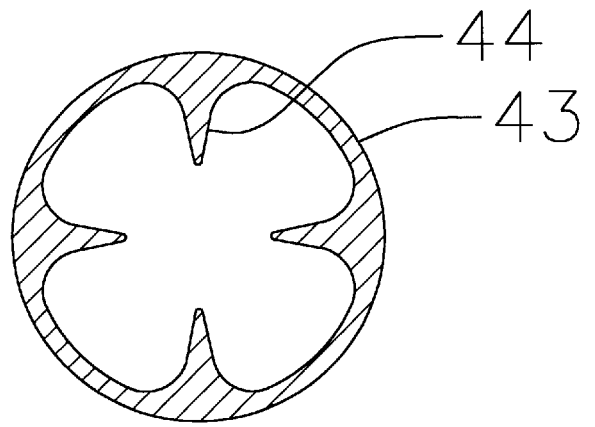
FIG. 3 is a cross-sectional view taken along line 3—3 of FIG. 1.
Figure 4:
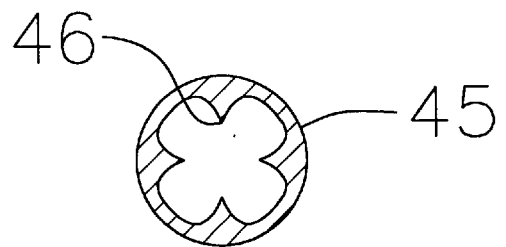
FIG. 4 is a cross-sectional view taken along line 3—3 of FIG. 1.

Referring to FIGS. 3 and 4, the plurality of first and second protrusions 44, 46 are respectively formed in embossed shape so as to create a laminar flow when the cooling air passes over the respective first and second protrusions 44, 46.

Figure 5:
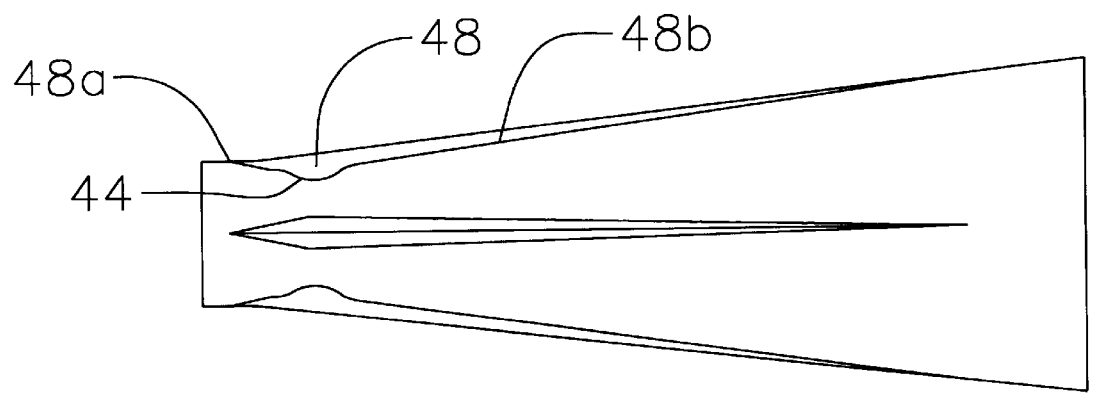
FIG. 5 is a partial cross-sectional view detailing a protrusion structure according to the present invention.
Figure 6:
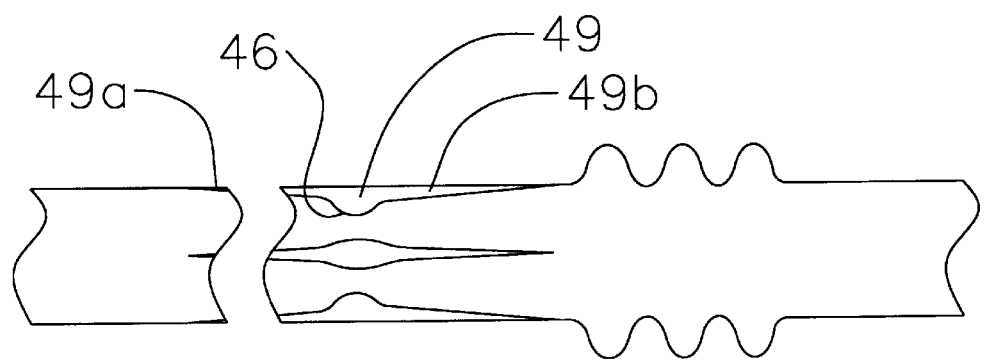
FIG. 6 is a partial cross-sectional view detailing another protrusion structure according to the present invention.

As further shown in FIGS. 5 and 6, each base 48, 49 of the plurality of first and second embossed protrusions 44, 46 comprises a front base end 48a, 49a and a rear base end 48b, 49b Here, the front base end 48a, 49a is decrementally enlongated toward the first horn end 18, and the rear base end 48b, 49b is also decrementally elongated toward the second horn end 20, thereby reliably sustaining the protrusions 44, 46 while generating a laminar flow when the cooling air is provided into the housing 22. In particular, the second base ends 48b, 49b decrease at a slower rate than the first base ends 48a, 49a so that the second base ends 48b, 49b are elongated further than the first base end 48a, 49a.

Also, the housing 22 may have a first crimple zone 30 between the first periphery 43 and the second periphery 45. Selectively, the first crimple zone 30 may be formed outside the second periphery toward the operative tip 16. The housing 22 may further have a second crimple zone 32 so that the first and second crimple zones 30, 32 can be formed outside the second periphery 45 toward the operative tip 16. Here, the crimple zones 30, 32 serve to protect the operative tip 16 while providing flexibility during operation.

In another embodiment of the present invention, the air cooled ultrasonic apparatus 10 comprises a horn cover 21 having an air outlet 26, and a housing 22 having an air inlet 24. The horn cover 21 is engagedly attached to the housing 22. The horn cover 21 may further comprise a first periphery 43 and a second periphery 45, wherein a plurality of first protrusions 44 radially extend from the first periphery 43 and a plurality of second protrusions 46 radially extend from the second periphery 45. As a result, the cooling air provided into the housing 22 through the inlet 24 passes over the respective first and second protrusions while creating a laminar flow which enables more efficient cooling operation than a boundary flow. Here, the horn cover 21 may be formed of one selected from a silicon rubber, a plastic material, a fabric material and other commonly known material.

The horn cover 21 may have a first crimple zone 30 between the first periphery 43 and the second periphery 45. The first crimple zone 30 may be selectively formed outside the second periphery 45 toward the operative tip 16. The horn cover 21 may further include a second crimple zone 32 and the first and second crimple zones 30, 32 may be selectively formed outside the second periphery 45 toward the operative tip 16.

Specifically, the cooling air is supplied into the apparatus 10 through the air inlet 24 formed through a rear end 23 of the housing 22 opposed to the operative tip 16 and discharged through the air outlet 26 formed through the peripheral opening 27 between the operative tip 16 and the front end 25 of the horn cover. Selectively, the air outlet 26 may be formed adjacent to the front end 25 of the horn cover 21.

Likewise, the respective constructions of the first and second embodiments of the present invention are similar except that the second embodiment further includes the horn cover 21.

The air cooled ultrasonic apparatus as described above can be applied to medical, dental or plastic surgery, such as for drilling, nailing, cutting and suturing operation, and to industrial use, such as for drilling and nailing operation.

The advantages of the present invention are numerous. First, the air cooling system applied to the air cooled ultrasonic apparatus according to the present invention is highly efficient compared to the prior art because a wider surface area between the elongated horn 14, the horn cover 21 and the housing 22 than the surface area of a conventional cooling water hollow hole formed though the horn, can be exposed to the cooling air, thereby enhancing cooling efficiency. That is, an ultrasonic energy becomes decreased in proportion that a cooling surface area becomes larger. This is because an energy transit is influenced by the ratio of stress and thickness of the horn.

Second, the present invention enables a cooling air to be controlled as low as a below zero Celsius degree, that is, below a freezing point, thereby maximizing a cooling effect.

Third, various bits can be applied since the present invention has overcome the conventional water draining problem around the operative tip, and even the air outlet can be formed in a desired portion of the horn cover.

Fourth, since impedance Z (=ρ·c) for air is less than impedance Z' (=ρ'·c') for water (where, ρ denotes density, c denotes velocity), that is, ρ·c<ρ'·c' is satisfied, the cooling air enables a low c at a cold temperature without being influenced by atmospheric pressure, thereby further realizing better cooling performance.

Although the invention has been described in considerable detail with reference to certain preferred versions thereof, other versions are possible by converting the aforementioned construction. Therefore, the scope of the invention shall not be limited by the specification specified above and the appended claims.

What is claimed is:

1. An air cooled ultrasonic apparatus, comprising:
   a) a housing having an air inlet, an air outlet, a first periphery, and a second periphery;
   b) a plurality of first protrusions radially extending from the first periphery;
   c) a plurality of second protrusions radially extending from the second periphery;
   d) a piezoelectric transducer means attached to the housing; and
   e) an elongated horn having a first horn end and a second horn end, wherein the first horn end forms an operative tip, wherein the second horn end is attached to the transducer means and housed in the housing, wherein the elongated horn is operably supported by the first and second protrusions, and wherein a cooling air is supplied through the air inlet into the housing and discharged through the air outlet.

2. The apparatus of claim 1, wherein the plurality of first and second protrusions are respectively formed in embossed shape so as to create a laminar flow when the cooling air passes over the respective first and second protrusions.

3. The apparatus of claim 2, wherein each base of the plurality of first and second embossed protrusions comprises a front base end and a rear base end, wherein the front base end is decrementally enlongated toward the first horn end, and wherein the rear base end is decrementally elongated toward the second horn end.

4. The apparatus of claim 3, wherein the second base end is elongated further than the first base end.

5. The apparatus of claim 1, wherein the housing further comprises a first crimple zone, and wherein the first crimple zone is formed between the first periphery and the second periphery.

6. The apparatus of claim 5, wherein the first crimple zone is formed outside the second periphery toward the operative tip.

7. The apparatus of claim 5, wherein the horn cover further comprises a second crimple zone, wherein the first and second crimple zones are formed outside the second periphery toward the operative tip.

8. The apparatus of claim 1, wherein the air inlet is formed through a rear end of the housing opposed to the operative tip, and wherein the air outlet is formed through a peripheral opening between the operative tip and a front end of the housing.

9. The apparatus of claim 8, wherein the air outlet is formed adjacent to the front end of the housing.

10. An air cooled ultrasonic apparatus, comprising:
    a) a housing having an air inlet;
    b) a horn cover having an air outlet, a first periphery and a second periphery, wherein the horn cover is engagedly attached to the housing;
    c) a plurality of first protrusions radially extending from the first periphery;
    d) a plurality of second protrusions radially extending from the second periphery;
    e) a piezoelectric transducer means attached to the housing;
    f) an elongated horn having a first horn end and a second horn end, wherein the horn cover flexibly receives the first horn forming an operative tip, wherein the second horn end is attached to the transducer means and housed in the housing, wherein the elongated horn is operably supported by the first and second protrusions, and wherein a cooling air is supplied through the air inlet into the housing and discharged through the air outlet of the horn cover.

11. The apparatus of claim 10, wherein the plurality of first and second protrusions are respectively formed in embossed shape so as to create a laminar flow when the cooling air passes over the respective first and second protrusions.

12. The apparatus of claim 11, wherein each base of the plurality of first and second embossed protrusions comprises a front base end and a rear base end, wherein the front base end is decrementally enlongated toward the first horn end, and wherein the rear base end is decrementally elongated toward the second horn end.

13. The apparatus of claim 12, wherein the second base end is elongated further than the first base end.

14. The apparatus of claim 10, wherein the horn cover further comprises a first crimple zone, and wherein the first crimple zone is formed between the first periphery and the second periphery.

15. The apparatus of claim 14, wherein the first crimple zone is formed outside the second periphery toward the operative tip.

16. The apparatus of claim 14, wherein the horn cover further comprises a second crimple zone, wherein the first and second crimple zones are formed outside the second periphery toward the operative tip.

17. The apparatus of claim 10, wherein the air inlet is formed through a rear end of the housing opposed to the operative tip, and wherein the air outlet is formed through a peripheral opening between the operative tip and a front end of the horn cover.

18. The apparatus of claim 17, wherein the air outlet is formed adjacent to the front end of the horn cover.

* * * * *